(12) United States Patent
Tateishi et al.

(10) Patent No.: US 9,237,856 B2
(45) Date of Patent: Jan. 19, 2016

(54) LIGHT DETECTING APPARATUS AND FLUID MEASURING APPARATUS

(75) Inventors: Kiyoshi Tateishi, Hannou (JP); Atsuya Ito, Yokohama (JP); Yoshinori Kimura, Hanno (JP)

(73) Assignee: PIONEER CORPORATION, Kanagawa (JP)

( * ) Notice: Subject to any disclaimer, the term of this patent is extended or adjusted under 35 U.S.C. 154(b) by 482 days.

(21) Appl. No.: 13/805,262

(22) PCT Filed: Jun. 24, 2010

(86) PCT No.: PCT/JP2010/060765
§ 371 (c)(1),
(2), (4) Date: Dec. 18, 2012

(87) PCT Pub. No.: WO2011/161799
PCT Pub. Date: Dec. 29, 2011

(65) Prior Publication Data
US 2013/0090564 A1    Apr. 11, 2013

(51) Int. Cl.
*A61B 8/00*    (2006.01)
*A61B 5/026*    (2006.01)
*G01F 1/66*    (2006.01)
*G01P 5/26*    (2006.01)
*G01S 17/58*    (2006.01)

(52) U.S. Cl.
CPC .............. *A61B 5/0261* (2013.01); *G01F 1/661* (2013.01); *G01F 1/663* (2013.01); *G01F 1/667* (2013.01); *G01P 5/26* (2013.01); *G01S 17/58* (2013.01)

(58) Field of Classification Search
CPC ...... A61B 5/055; A61B 5/0261; G01F 1/661; G01F 1/667; G01F 1/663; G01S 17/58
See application file for complete search history.

(56) References Cited

U.S. PATENT DOCUMENTS

| | | |
|---|---|---|
| 4,873,989 A | 10/1989 | Einzig |
| 5,410,145 A | 4/1995 | Coroy |
| 5,588,437 A | 12/1996 | Byrne |
| 6,198,951 B1 | 3/2001 | Kosuda et al. |
| 6,459,919 B1 * | 10/2002 | Lys et al. ..................... 600/407 |

(Continued)

FOREIGN PATENT DOCUMENTS

| | | |
|---|---|---|
| EP | 0941694 A1 | 9/1999 |
| JP | 50-161080 | 12/1975 |

(Continued)

OTHER PUBLICATIONS

EESR dated May 9, 2014; Application No. 10853659.0.

(Continued)

*Primary Examiner* — Joel Lamprecht
(74) *Attorney, Agent, or Firm* — Young & Thompson

(57) ABSTRACT

A light detecting apparatus includes: a first photoelectric conversion element unit (110) and a second photoelectric conversion element unit (120) each of which converts input light to an electric current and output it; an optical current transducer unit (100) for outputting, as a detected current, a differential current between an electric current outputted by the first photoelectric conversion element unit and an electric current outputted by the second photoelectric conversion element unit; and a first current/voltage converting unit (200) for amplifying the detected current outputted from the optical current transducer unit, converting it to a voltage signal, and outputting the voltage signal.

10 Claims, 10 Drawing Sheets

(56) References Cited

U.S. PATENT DOCUMENTS

| | | |
|---|---|---|
| 6,584,566 B1 | 6/2003 | Hardjono |
| 6,813,714 B1 | 11/2004 | Hardjono et al. |
| 7,945,272 B2 | 5/2011 | Kim |
| 2003/0044020 A1 | 3/2003 | Aboba et al. |
| 2003/0177267 A1 | 9/2003 | Orava et al. |
| 2005/0083397 A1 | 4/2005 | Matsuda |
| 2006/0063548 A1 | 3/2006 | Kim |
| 2007/0071021 A1 | 3/2007 | Girao |
| 2010/0011063 A1 | 1/2010 | Blaiotta et al. |

FOREIGN PATENT DOCUMENTS

| | | |
|---|---|---|
| JP | 60-213804 A | 10/1985 |
| JP | 06-224652 | 8/1994 |
| JP | 2000-323940 | 11/2000 |
| JP | 3313841 | 8/2002 |
| JP | 2006-081184 | 3/2006 |
| JP | 2007-089156 | 4/2007 |
| JP | 2007-175415 | 7/2007 |
| JP | 2008-257340 | 10/2008 |
| JP | 2008-543137 | 11/2008 |
| JP | 2009-039568 | 2/2009 |
| WO | 90/11044 A1 | 10/1990 |
| WO | WO 99/12469 | 3/1999 |
| WO | 2007/009541 | 1/2007 |
| WO | WO2007/072814 | 6/2007 |

OTHER PUBLICATIONS

European Search Report—EP 14 19 4613—Mar. 17, 2015.
International Search Report, PCT/JP2010/060765, Jul. 27, 2010.

* cited by examiner

LIGHT DETECTING APPARATUS AND FLUID MEASURING APPARATUS

TECHNICAL FIELD

The present invention relates to, for example, a light detecting apparatus for detecting a signal light component included in light which is reflected, scattered, or the like by a test object, a specimen, or an object to be examined, and a fluid measuring apparatus, such as a laser Doppler blood flowmeter, provided with the light detecting apparatus.

BACKGROUND ART

As this type of light detecting apparatus, for example, there is an apparatus used as a light receiving unit for detecting light from a living body on a laser Doppler blood flowmeter (e.g. refer to patent documents 1 and 2). The laser Doppler blood flowmeter irradiates the living body with light such as laser light, and calculates blood flow velocity or the like of the living body from a change in wavelength due to a Doppler shift in the light reflection or scattering. The light detecting apparatus used as the light receiving unit of the laser Doppler blood flowmeter is typically provided with: a photoelectric conversion element such as a photodiode; and a current/voltage conversion circuit including an operational amplifier (i.e. "operational amplification circuit") for amplifying an output electric current of the photoelectric conversion element and converting it to a voltage signal.

On the other hand, for example, a patent document 3 discloses that on a light receiving circuit used for optical communication or the like, bias elements are connected to both ends of a photodiode and the both ends are connected to an input end of a differential amplifier (operational amplifier) via a condenser and that resistive elements are provided between a positive output and a negative input and between an inverted output and a positive input of the differential.

PRIOR ART DOCUMENT

Patent Document

Patent document 1: Japanese Patent Application Laid Open No. 2007-175415
Patent document 2: Japanese Patent No. 3313841
Patent document 3: Japanese Patent Application Laid Open No. Hei 6-224652

DISCLOSURE OF INVENTION

Subject to be Solved by the Invention

If this type of light detecting apparatus is used as the light receiving unit of the laser Doppler blood flowmeter as described above, there is such a technical problem that it is hard to accurately detect a signal light component because intensity of the signal light component included in the light reflected or scattered by the living body (i.e. a Doppler-shifted modulation component) is less than that of a fixed light component included in the light reflected or scattered by the living body (i.e. a component which is not changed by the reflection or scattering by the living body).

In view of the aforementioned problems, it is therefore an object of the present invention to provide a light detecting apparatus capable of accurately detecting a signal light component included in light which is reflected, scattered, or the like by a test object, and a fluid measuring apparatus provided with such a light detecting apparatus.

Means for Solving the Subject

The above object of the present invention can be achieved by a light detecting apparatus for detecting a signal light component included in input light, the light detecting apparatus provided with: an optical current transducer unit which includes first and second photoelectric conversion element units each converting the input light to an electric current and outputting it, and which outputs a differential current between an electric current outputted by the first photoelectric conversion element unit and an electric current outputted by the second photoelectric conversion element unit as a detected current; and a first current/voltage converting unit which amplifies the detected current outputted from the optical current transducer unit, converts it to a voltage signal, and outputs the voltage signal.

The above object of the present invention can be also achieved by a fluid measuring apparatus provided with: an irradiating unit for irradiating a test object with light; the light detecting apparatus of the present invention described above to which light from the test object due to the irradiated light is inputted as the input light; and a calculating unit for calculating fluid information about a fluid in the test object on the basis of the voltage signal outputted by the first current/voltage converting unit.

The operation and other advantages of the present invention will become more apparent from Mode for Carrying Out the Invention explained below.

MODE FOR CARRYING OUT THE INVENTION

Figure 1:
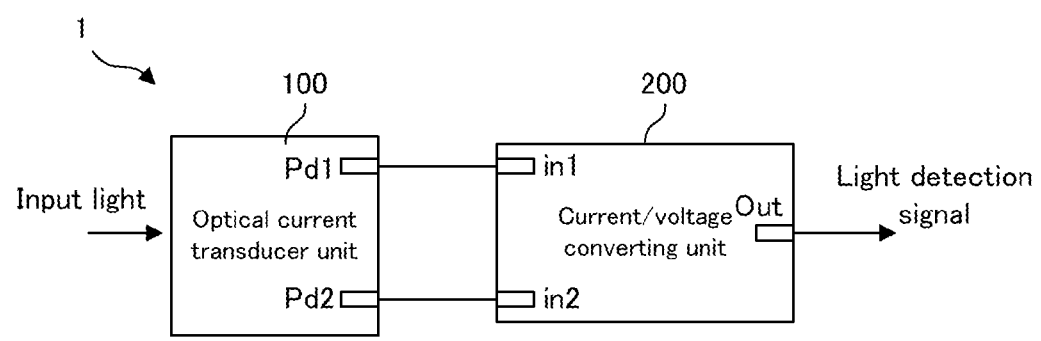
FIG. 1 is a block diagram conceptually showing an entire configuration of a light detecting apparatus in a first example.

Hereinafter, embodiments of the present invention will be explained.

The above object according to a first embodiment can be achieved by a light detecting apparatus for detecting a signal light component included in input light, the light detecting apparatus provided with: an optical current transducer unit which includes first and second photoelectric conversion element units each converting the input light to an electric current and outputting it, and which outputs a differential current between an electric current outputted by the first photoelectric conversion element unit and an electric current outputted by the second photoelectric conversion element unit as a detected current; and a first current/voltage converting unit which amplifies the detected current outputted from the optical current transducer unit, converts it to a voltage signal, and outputs the voltage signal.

According to the light detecting apparatus in the first embodiment, in its operation, for example, light which is reflected, scattered, or the like by a test object, a specimen, or an object to be examined is inputted to the optical current transducer unit as the input light. The input light inputted to the optical current transducer unit is transduced by the optical current transducer unit to the electric current and is outputted as the detected current. The detected current outputted from the optical current transducer unit is amplified with a predetermined gain by the first current/voltage converting unit including, for example, an operational amplifier and a negative feedback resistor, and is converted to the voltage signal. On the basis of the voltage signal outputted by the first current/voltage converting unit, the signal light component included in the input light (e.g. a modulation component by the reflection, scattering, or the like in the test object) can be detected.

Particularly in the embodiment, the optical current transducer unit includes the first and second photoelectric conversion element units each converting the input light to the electric current and outputting it, and outputs the differential current between the electric current outputted by the first photoelectric conversion element unit and the electric current outputted by the second photoelectric conversion element unit as the detected current.

Specifically, each of the first and second photoelectric conversion element units is composed of one or a plurality of photoelectric conversion element units (e.g. photodiodes, etc.) and outputs the electric current in accordance with amount of the input light. The optical current transducer unit outputs the differential current between the electric current outputted by the first photoelectric conversion element unit and the electric current outputted by the second photoelectric conversion element unit as the detected current. For example, the first and second photoelectric conversion element units are connected in parallel such that a cathode of the first photoelectric conversion element unit and an anode of the second photoelectric conversion element unit are connected and such that an anode of the first photoelectric conversion element unit and a cathode of the second photoelectric conversion element unit are connected. Incidentally, the cathode of the first photoelectric conversion element unit means an electrode into which the electric current flows from the exterior when the input light is inputted to the first photoelectric conversion element unit, and the anode of the first photoelectric conversion element unit means an electrode from which the electric current flows out to the exterior when the input light is inputted to the first photoelectric conversion element unit. In the same manner, the cathode of the second photoelectric conversion element unit means an electrode into which the electric current flows from the exterior when the input light is inputted to the second photoelectric conversion element unit, and the anode of the second photoelectric conversion element unit means an electrode from which the electric current flows out to the exterior when the input light is inputted to the second photoelectric conversion element unit. Alternatively, for example, the first and second photoelectric conversion element units are connected in series such that cathodes thereof or anodes thereof are connected to each other.

Thus, of the electric current outputted from each of the first and second photoelectric conversion element units, an electric current component corresponding to a fixed light component included in the input light (hereinafter referred to as a direct current (DC) component as occasion demands) can be reduced or eliminated, and an electric current component corresponding to the signal light component included in the input light (hereinafter referred to as an alternate or alternating current (AC) component as occasion demands) can be outputted as the detected current. In other words, it is possible to cancel the DC component of the electric current outputted from the first photoelectric conversion element unit and the DC component of the electric current outputted from the second photoelectric conversion element unit, and it is also possible to output the detected current mainly including the AC component corresponding to the signal light component included in the input light.

Therefore, it is possible to increase the gain when the detected current is amplified and converted to the voltage signal by the first current/voltage converting unit. In other words, according to the embodiment, as described above, since the DC component of the electric current outputted from the first photoelectric conversion element unit and the DC component of the electric current outputted from the second photoelectric conversion element unit are canceled and the detected current hardly includes or does not include the DC component at all, it is possible to increase the gain of the amplification by the first current/voltage converting unit while avoiding occurrence of a saturation phenomenon of the first current/voltage converting unit which can occur, for example, if the DC component included in the detected current is relatively large (e.g. a saturation phenomenon of an operational amplifier included in the first current/voltage converting unit). Incidentally, the saturation phenomenon of the first current/voltage converting unit means such a phenomenon that the voltage signal outputted by the first current/voltage converting unit becomes a constant saturation voltage determined in accordance with a power supply voltage of the first current/voltage converting unit regardless of a current value of the detected current if the current value of the detected current inputted to the first current/voltage converting unit is greater than a predetermined current value.

Moreover, according to the embodiment, as described above, since the electric current mainly including the AC component corresponding to the signal light component included in the input light can be outputted as the detected current, it is possible to improve a signal-to-noise (S/N) ratio in the voltage signal outputted by the first current/voltage converting unit. In other words, according to the embodiment, of the electric current outputted from each of the first and second photoelectric conversion element units, the DC component corresponding to a noise component included in the input light as the fixed light component is reduced or eliminated, and the detected current mainly including the AC component corresponding to the signal light component is outputted. Thus, it is possible to improve the S/N ratio in the voltage signal outputted by the first current/voltage converting unit.

As a result, according to the light detecting apparatus in the embodiment, the signal light component included in the input light can be detected, accurately.

In one aspect of the light detecting apparatus in the first embodiment, the first and second photoelectric conversion element units are connected in parallel such that a cathode of the first photoelectric conversion element unit and an anode of the second photoelectric conversion element unit are connected and such that an anode of the first photoelectric conversion element unit and a cathode of the second photoelectric conversion element unit are connected.

According to this aspect, the differential current between the electric current outputted by the first photoelectric conversion element unit and the electric current outputted by the second photoelectric conversion element unit can be certainly outputted as the detected current.

In another aspect of the light detecting apparatus in the first embodiment, the first and second photoelectric conversion element units are connected in series such that cathodes thereof or anodes thereof are connected to each other.

According to this aspect, the differential current between the electric current outputted by the first photoelectric conversion element unit and the electric current outputted by the second photoelectric conversion element unit can be certainly outputted as the detected current.

In the aspect in which the first and second photoelectric conversion element units are connected in series, the light detecting apparatus is further provided with a bias voltage applying device which is connected between the first and second photoelectric conversion element units connected in series and which can apply a bias voltage to each of the first and second photoelectric conversion element units, and the optical current transducer unit outputs each of the electric current outputted by the first photoelectric conversion element unit and the electric current outputted by the second photoelectric conversion element unit if the bias voltage is applied to each of the first and second photoelectric conversion element units by the bias voltage applying device.

In this case, it is possible to detect the DC component of each of the electric current outputted by the first photoelectric conversion element unit and the electric current outputted by the second photoelectric conversion element unit. Thus, it is possible to calculate a ratio of the signal light component with respect to the fixed light component included in the input light. Therefore, the signal light component included in the input light can be detected, more accurately.

In another aspect of the light detecting apparatus in the first embodiment, it is further provided with: a third photoelectric conversion element unit for converting the input light to an electric current and outputting it; and a second current/voltage converting unit for amplifying the electric current outputted from the third photoelectric conversion element unit and converting it to a voltage signal.

According to this aspect, on the basis of the voltage signal outputted from the second current/voltage converting unit, the DC component of the electric current outputted by the third photoelectric conversion element unit can be detected. Thus, it is possible to calculate the ratio of the signal light component with respect to the fixed light component included in the input light. Therefore, the signal light component included in the input light can be detected, more accurately.

In another aspect of the light detecting apparatus in the first embodiment, the optical current transducer unit has first and second terminals which are connected to both ends of the first and second photoelectric conversion element units, respectively, and the first current/voltage converting unit has: a fully differential amplifier having a positive input terminal connected to the first terminal, a negative input terminal connected to the second terminal, a negative output terminal for inverting, amplifying, and outputting a signal inputted to the positive input terminal, and a positive output terminal for inverting, amplifying, and outputting a signal inputted to the negative input terminal; a first negative feedback resistor connected between the positive input terminal and the negative output terminal; a second negative feedback resistor connected between the negative input terminal and the positive output terminal; and an amplifier for amplifying a difference between a signal outputted from the positive output terminal and a signal outputted from the negative output terminal and for outputting it as a voltage signal.

According to this aspect, the first and second photoelectric conversion element units, such as photodiodes, can be operated in a condition that a reverse bias voltage is hardly or not applied at all, i.e. in a so-called power generation mode. Thus, it is possible to reduce or eliminate a dark current generated in the first and second photoelectric conversion element units (i.e. an opposite direction current generated by the reverse bias voltage even without the input light inputted). This makes it possible to reduce a noise current due to fluctuation of the dark current and to improve the S/N ratio in the voltage signal outputted by the amplifier of the first current/voltage converting unit. As a result, the signal light component included in the input light can be detected, more accurately.

The above object according to the first embodiment can be also achieved by a fluid measuring apparatus provided with: an irradiating unit for irradiating a test object with light; the light detecting apparatus according to the aforementioned embodiment (including its various aspects) to which light from the test object due to the irradiated light is inputted as the input light; and a calculating unit for calculating fluid information about a fluid in the test object on the basis of the voltage signal outputted by said first current/voltage converting unit.

According to the fluid measuring apparatus in the embodiment, since it is provided with the light detecting apparatus according to the aforementioned embodiment, it is possible to accurately calculate the fluid information about the fluid in the test object.

EXAMPLES

Hereinafter, examples of the present invention will be explained with reference to the drawings.

First Example

A light detecting apparatus in a first example will be explained with reference to FIG. 1 to FIG. 3.

Firstly, a configuration of the light detecting apparatus in the first example will be explained with reference to FIG. 1 and FIG. 2.

FIG. 1 is a block diagram conceptually showing an entire configuration of the light detecting apparatus in the first example. FIG. 2 is a block diagram showing a configuration of the light detecting apparatus in the first example.

Figure 2:
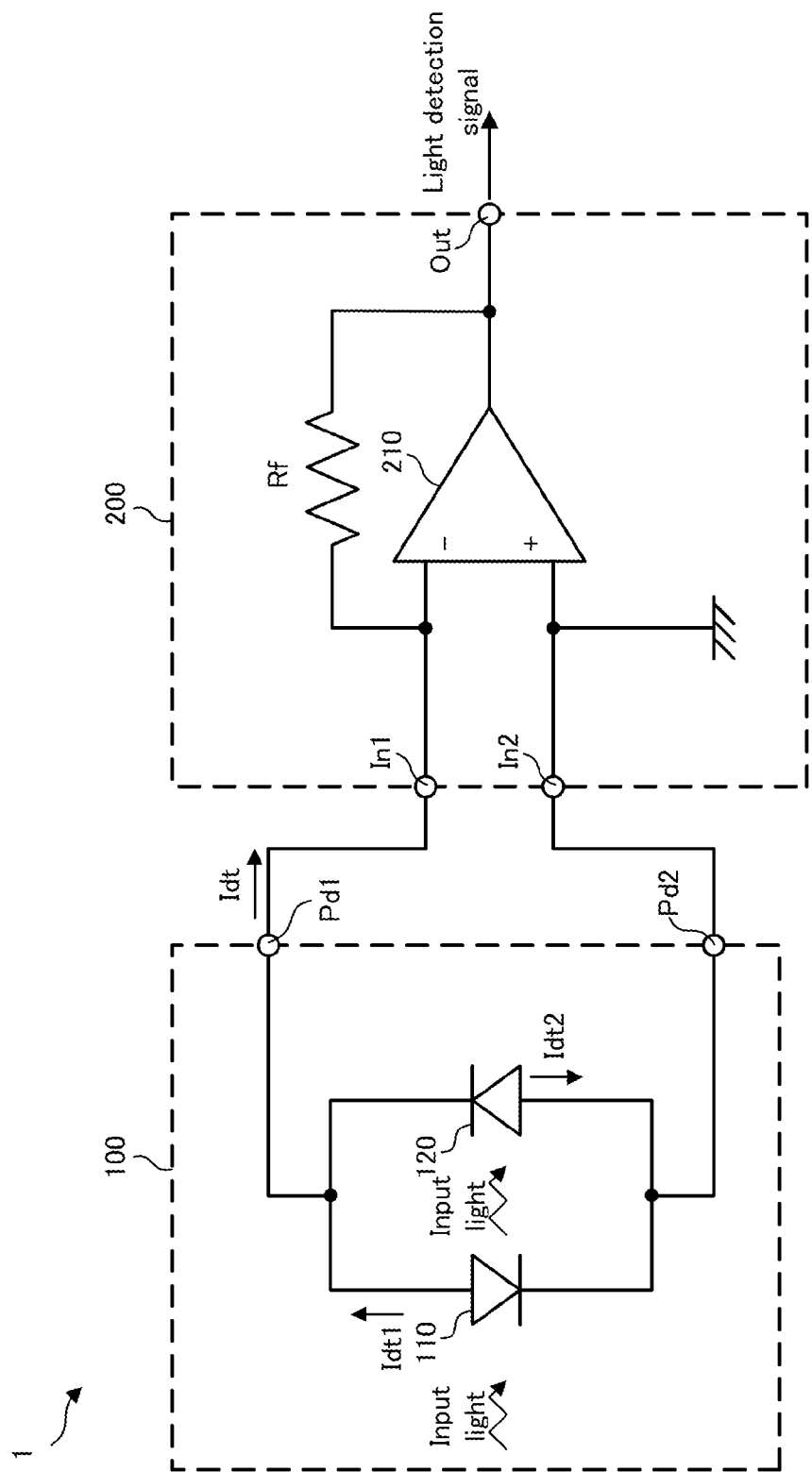
FIG. 2 is a block diagram showing a configuration of the light detecting apparatus in the first example.

In FIG. 1 and FIG. 2, a light detecting apparatus 1 in the first example is a light detecting apparatus for detecting a signal light component included in input light inputted from the exterior, which is provided with: an optical current transducer unit 100; and a current/voltage converting unit 200. The input light is, for example, light obtained by that laser light is reflected, scattered, or the like by a test object, a specimen, or an object to be examined (e.g. a human finger, etc.) and includes the signal light component indicating information about the test object (e.g. a modulation component by the reflection, scattering, or the like in the test object).

In FIG. 2, the optical current transducer unit 100 has light receiving elements 110 and 120 and terminals Pd1 and Pd2. Incidentally, the light receiving element 110 is one example of the "first photoelectric conversion element unit" of the present invention, and the light receiving element 120 is one example of the "second photoelectric conversion element unit" of the present invention.

Each of the light receiving elements 110 and 120 is a photodiode such as a P-Intrinsic-N (PIN) diode, receives input light, and outputs an electric current in accordance with amount of the input light received. The light receiving elements 110 and 120 are connected in parallel such that a cathode of the light receiving element 110 (in other words, an N-type semiconductor of the light receiving element 110) and an anode of the light receiving element 120 (in other words, a P-type semiconductor of the light receiving element 120) are connected to each other and such that an anode of the light receiving element 110 (in other words, a P-type semiconductor of the light receiving element 110) and a cathode of the light receiving element 120 (in other words, an N-type semiconductor of the light receiving element 120) are connected to each other. The anode of the light receiving element 110 and the cathode of the light receiving element 120 are connected to the terminal Pd1, and the cathode of the light receiving element 110 and the anode of the light receiving element 120 are connected to the terminal Pd2. Since the light receiving elements 110 and 120 are connected in parallel in this manner, the optical current transducer unit 100 can output a differential current between an electric current Idt1 outputted by the light receiving element 110 and an electric current Idt2 outputted by the light receiving element 120 as a detected current Idt from the terminal Pd1.

The terminals Pd1 and Pd2 are connected to input terminals In1 and In2 of the current/voltage converting unit 200 described later, respectively.

The current/voltage converting unit 200 has: the input terminals In1 and In2; an operational amplifier 210; a feedback resistor Rf; and an output terminal Out. The current/voltage converting unit 200 is configured as a transimpedance amplifier (current-voltage conversion amplifier) for converting an electric current inputted to the input terminal In1 to a voltage signal and outputting it. The current/voltage converting unit 200 converts the detected current Idt, which is inputted to the input terminal In1 from the optical current transducer unit 100, to the voltage signal and outputs it as a light detection signal from the output terminal Out.

The input terminal In1 is connected to an inverted input terminal (−) of the operational amplifier 210. The input terminal In2 is connected to a non-inverted input terminal (+) of the operational amplifier 210. The input terminal In2 and the non-inverted input terminal of the operational amplifier 210 are grounded (i.e. connected to a reference potential such as a ground (GND) potential).

The feedback resistor Rf is connected between an output terminal of the operational amplifier 210 and the inverted input terminal of the operational amplifier 210, performs negative feedback, and converts an electric current to a voltage. Since the negative feedback is performed by the feedback resistor Rf, a potential difference between the inverted input terminal and the non-inverted input terminal of the operational amplifier 210 is almost zero (i.e. a so-called "imaginary short" is realized).

The output terminal Out is connected to the output terminal of the operational amplifier 210. The output terminal Out outputs the voltage signal outputted from the operation amplifier 210 as the light detection signal.

Next, operations of the light detecting apparatus in the example will be explained with reference to FIG. 2.

In FIG. 2, in operation of the light detecting apparatus 1, if the input light is received by each of the light receiving elements 110 and 120, an electric current according to the amount of the input light is outputted from each of the light receiving elements 110 and 120. In other words, the light receiving element 110 outputs the electric current Idt1 in accordance with the amount of the input light received, and the light receiving element 120 outputs the electric current Idt2 in accordance with the amount of the input light received. Then, as described above, since the light receiving elements 110 and 120 are connected in parallel such that the cathode of the light receiving element 110 and the anode of the light receiving element 120 are connected to each other and such that the anode of the light receiving element 110 and the cathode of the light receiving element 120 are connected to each other, the differential current between the electric current Idt1 outputted from the light receiving element 110 and the electric current Idt2 outputted from the light receiving element 120 is outputted as the detected current Idt from the terminal Pd1.

Here, the input light includes the signal light component (e.g. the modulation component by the reflection, scattering, or the like in the test object) and a fixed light component (e.g. a noise component and a component according to the amount of the laser light applied or irradiated to the test object). Thus, each of the electric current Idt1 outputted by the light receiving element 110 and the electric current Idt2 outputted by the light receiving element 120 includes an AC component which is an electric current component corresponding to the signal light component included in the input light and a DC component which is an electric current component corresponding to the fixed light component included in the input light. The signal light component of the input light inputted to the light receiving element 110 and the signal light component of the input light inputted to the light receiving element 120 have mutually different optical paths because a position at which the light receiving element 110 is placed and a position at which the light receiving element 120 is placed are different from each other. Thus, the electric current components corresponding to the signal light components are signals having a low correlation with each other. Thus, the AC component of the electric current Idt1 outputted by the light receiving element 110 (i.e. the electric current component corresponding to the signal light component) and the AC component of the electric current Idt2 outputted by the light receiving element 120 have a low correlation with each other. In other words, the AC components of the electric currents Idt1 and Idt2 include many out-of-phase components having mutually different phases, amplitudes, and frequencies (in other words, uncorrelated components having a low correlation with one another). On the other hand, the DC component of the electric current Idt1 outputted by the light receiving element 110 (i.e. the electric current component corresponding to the fixed light component) and the DC component of the electric current Idt2 outputted by the light receiving element 120 have substantially the same amplitude if light receiving areas are set to be the same. In other words, the DC components of the electric currents Idt1 and Idt2 have in-phase components (in other words, correlated components having a strong correlation with each other).

Figure 3:
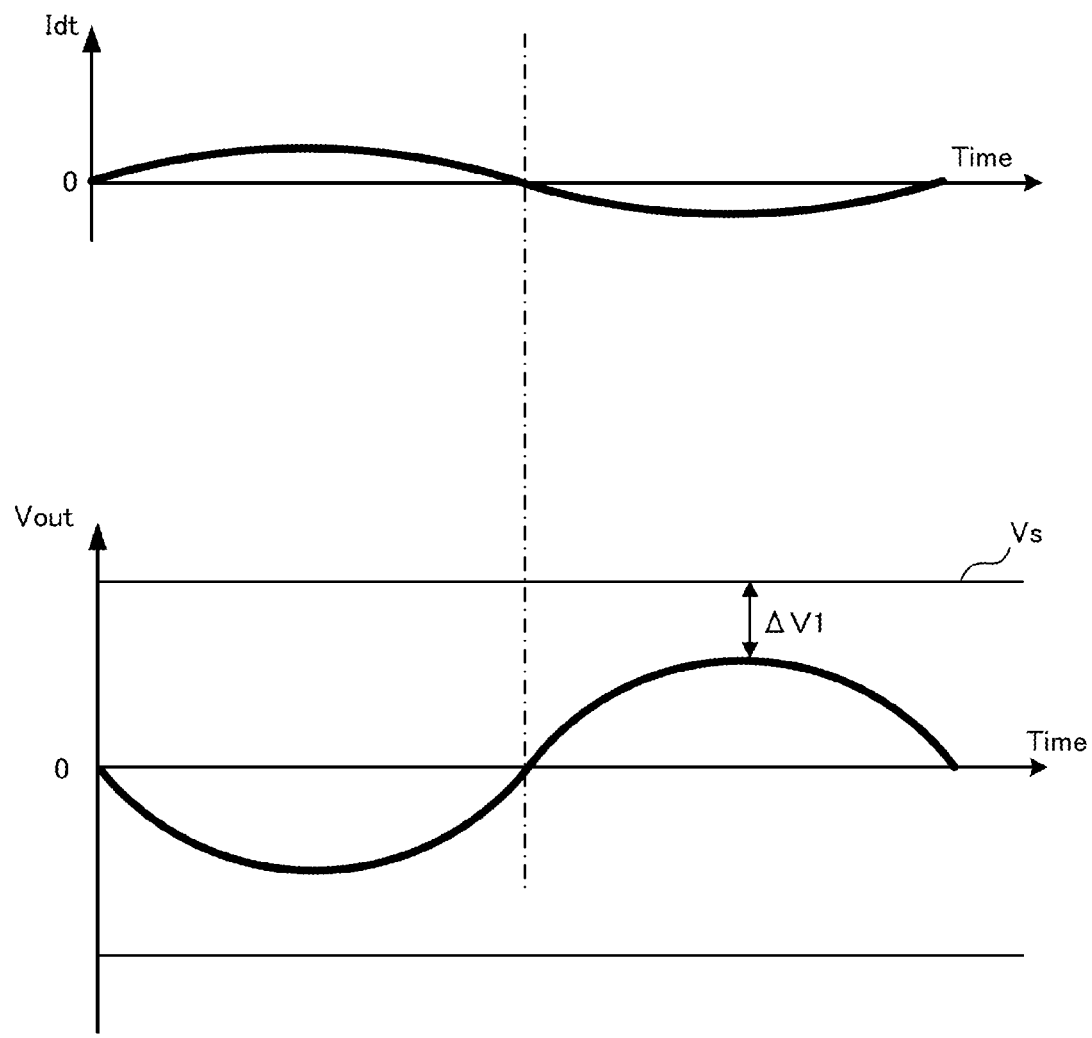
FIG. 3 is a waveform chart showing one example of each of a detected current Idt outputted from an optical current transducer unit of the light detecting apparatus in the first example and an output voltage Vout of an operational amplifier provided for a current/voltage converting unit.

Thus, as shown in FIG. 3, the detected current Idt, which is the differential current between the electric current Idt1 outputted from the light receiving element 110 and the electric current Idt2 outputted from the light receiving element 120, is an electric current which increases in comparison with the AC components of the electric currents Idt1 and Idt2 and in which the DC component is reduced or eliminated. Subtraction of signals including many uncorrelated components is equivalent to subtraction of random signals, and a signal power increases after the subtraction. Incidentally, FIG. 3 is a waveform chart showing one example of each of the detected current Idt and an output voltage Vout of the operational amplifier 210.

In other words, according to the optical current transducer unit 100, it is possible to cancel the DC component of the electric current Idt1 outputted by the light receiving element 110 and the DC component of the electric current Idt2 outputted by the light receiving element 120, and it is possible to output the detected current Idt mainly including the AC component corresponding to the signal light component included in the input light.

Therefore, it is possible to increase gain when the detected current Idt is amplified and converted to the voltage signal by the current/voltage converting unit 200. Saying it differently, according to the example, as described above, since the DC component of the electric current Idt1 outputted by the light receiving element 110 and the DC component of the electric current Idt2 outputted by the light receiving element 120 are canceled and the detected current Idt hardly includes or does not include the DC component at all, it is possible to increase the gain of the amplification by the current/voltage converting unit 200 while avoiding occurrence of a saturation phenomenon of the operational amplifier 210 included in the current/voltage converting unit 200 which can occur, for example, if the DC component included in the detected current Idt is relatively large. In other words, in FIG. 3, it is possible to increase the gain of the amplification by the current/voltage converting unit 200 while maintaining a relatively large difference $\Delta V1$ between a maximum value of the output voltage Vout of the operational amplifier 210 and a saturation voltage Vs of the operational amplifier 210.

Moreover, according to the example, as described above, since the optical current transducer unit 100 can output, as the detected current Idt, an electric current mainly including the AC component corresponding to the signal light component included in the input light, it is possible to improve an S/N ratio in the light detection signal outputted by the current/voltage converting unit 200. In other words, according to the example, the DC component corresponding to the noise component included as the fixed light component in the input light (e.g. the noise component due to fluctuation of a laser light source) is reduced or eliminated from the electric current Idt1 outputted by the light receiving element 110 and the electric current Idt2 outputted by the light receiving element 120, and the detected current Idt mainly including the AC component corresponding to the signal light component is outputted. Thus, it is possible to improve the S/N ratio in the light detection signal outputted by the current/voltage converting unit 200.

In addition, according to the example, as described above, the imaginary short is realized in which the potential difference between the inverted input terminal and the non-inverted input terminal of the operational amplifier 210 is almost zero. Thus, a potential difference between the terminal Pd1 connected to the inverted input terminal of the operational amplifier 210 via the input terminal In1 and the terminal Pd2 connected to the non-inverted input terminal of the operational amplifier 210 via the input terminal In2 is also almost zero, and each of the light receiving elements 110 and 120 can be operated in a zero bias condition (i.e. in a condition that a reverse bias voltage is hardly or not applied at all), i.e. in a so-called power generation mode. Therefore, it is possible to reduce or eliminate a dark current generated in the light receiving elements 110 and 120. This makes it possible to reduce a noise current due to fluctuation of the dark current and to improve the S/N ratio in the light detection signal outputted by the current/voltage converting unit 200.

According to the example, the DC component included as the fixed light component in the input light can be reduced or eliminated, and a ratio of the output voltage Vout as the output with respect to the detected current Idt as the input, i.e. a conversion gain, can be increased while the saturation phenomenon is avoided on the current/voltage converting unit 200. Thus, the S/N ratio can be improved.

Specifically, even if a resistance value of the feedback resistor Rf in FIG. 2 is set high, the saturation phenomenon of the operational amplifier 210 can be avoided. As one of main components of noise generated by the current/voltage converting unit 200, thermal noise of the feedback resistor Rf is well known. The thermal noise is proportional to the square root of the resistance value of the feedback resistor Rf. On the other hand, since the conversion gain is proportional to the resistance value of the feedback resistor Rf, if the resistance value of the feedback resistor Rf is set high, the S/N ratio is improved in multiples of the square root of the resistance value of the feedback resistor Rf. However, if the resistance value of the feedback resistor Rf is set high in a conventional simple photodiode configuration, the operational amplifier 210 is saturated by the DC component. If the operational amplifier 210 is saturated, the signal light component is not outputted, which causes fatal problems. On the other hand, according to the example, since the DC component can be reduced or eliminated at a stage of the detected current Idt, the operational amplifier 210 is not saturated even if the resistance value of the feedback resistor Rf is set high. Therefore, according to the example, it is possible to avoid the saturation of the operational amplifier 210 and to set the high S/N ratio by the high conversion gain at the same time.

As explained above, according to the light detecting apparatus 1 in the example, it is possible to improve the S/N ratio in the light detection signal outputted by the current/voltage converting unit 200. As a result, the signal light component included in the input light can be detected accurately.

Second Example

A light detecting apparatus in a second example will be explained with reference to FIG. 4.

Figure 4:
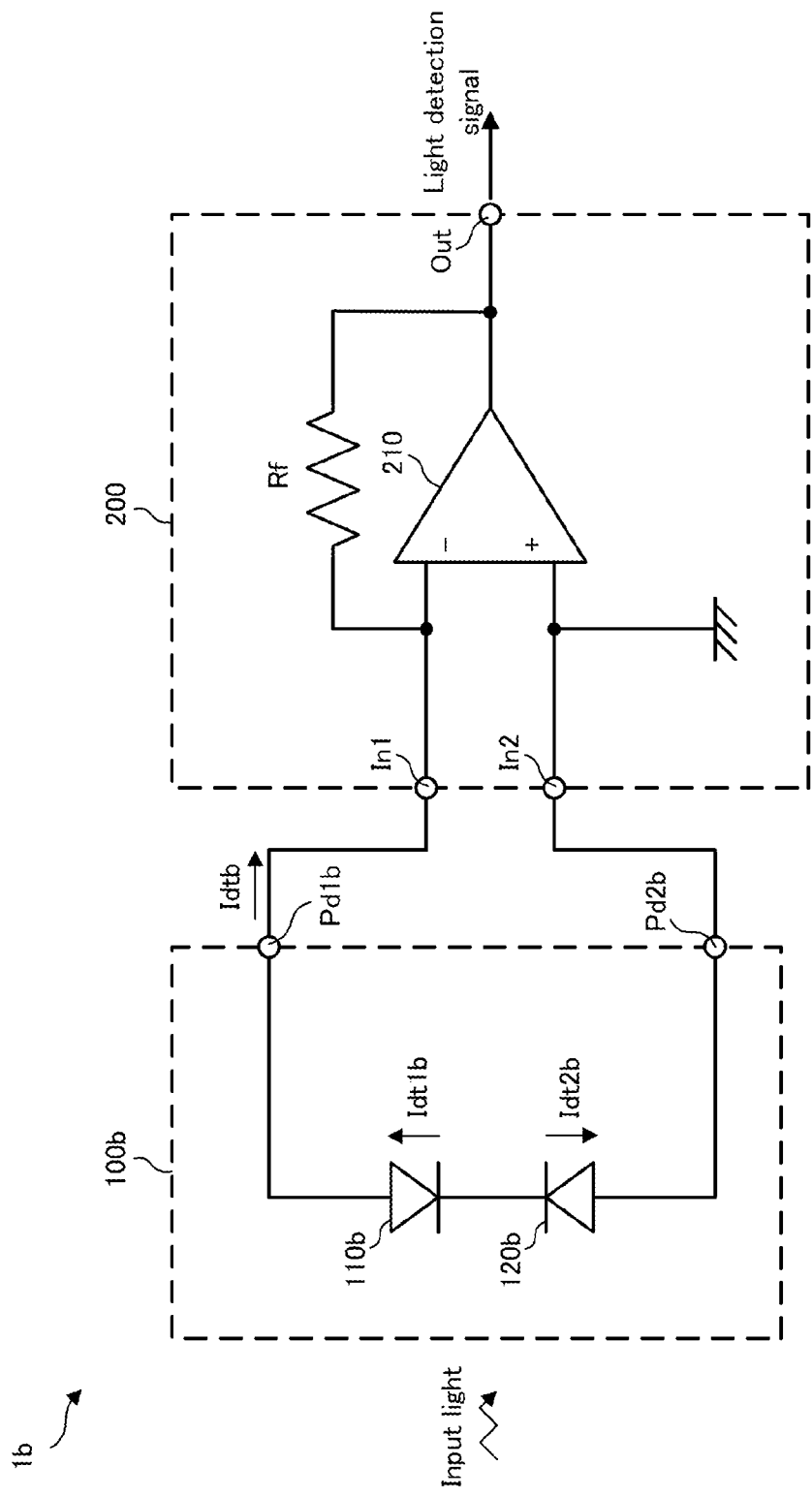
FIG. 4 is a block diagram showing a configuration of a light detecting apparatus in a second example.

FIG. 4 is a block diagram showing a configuration of the light detecting apparatus in the second example. Incidentally, in FIG. 4, the same constituents as those in the first example shown in FIG. 2 will carry the same reference numerals, and the explanation thereof will be omitted, as occasion demands.

In FIG. 4, a light detecting apparatus 1b in the second example is different from the light detecting apparatus 1 in the first example described above in that there is provided an optical current transducer unit 100b instead of the optical current transducer unit 100 in the first example described above; however, in other points, the light detecting apparatus 1b is configured in substantially the same manner as the light detecting apparatus 1 in the first example described above.

In FIG. 4, the optical current transducer unit 100b has light receiving elements 110b and 120b and terminals Pd1b and Pd2b. Incidentally, the light receiving element 110b is one example of the "first photoelectric conversion element unit" of the present invention, and the light receiving element 120b is one example of the "second photoelectric conversion element unit" of the present invention.

Each of the light receiving elements 110b and 120b is a photodiode such as a PIN diode, receives input light, and outputs an electric current in accordance with amount of the input light received. The light receiving elements 110b and 120b are connected in series such that cathodes thereof are connected to each other. An anode of the light receiving element 110b is connected to the terminal Pd1b, and an anode of the light receiving element 120b is connected to the terminal Pd2b. Since the light receiving elements 110b and 120b are connected in series in this manner, the optical current transducer unit 100b can output a differential current between an electric current Idt1b outputted by the light receiving element 110b and an electric current Idt2b outputted by the light receiving element 120b as a detected current Idtb from the terminal Pd1b.

The terminals Pd1b and Pd2b are connected to input terminals In1 and In2 of the current/voltage converting unit 200, respectively.

By virtue of the light detecting apparatus 1b configured in this manner, it is possible to receive the same benefits as those obtained by the light detecting apparatus 1 in the first example described above. In other words, it is possible to cancel a DC component of the electric current Idt1b outputted by the light receiving element 110b and a DC component of the electric current Idt2b outputted by the light receiving element 120b, and it is possible to output the detected current Idtb mainly including an AC component corresponding to a signal light component included in the input light. As a result, it is possible to improve an S/N ratio in a light detection signal outputted by the current/voltage converting unit 200.

Third Example

A light detecting apparatus in a third example will be explained with reference to FIG. 5 and FIG. 6.

Figure 5:
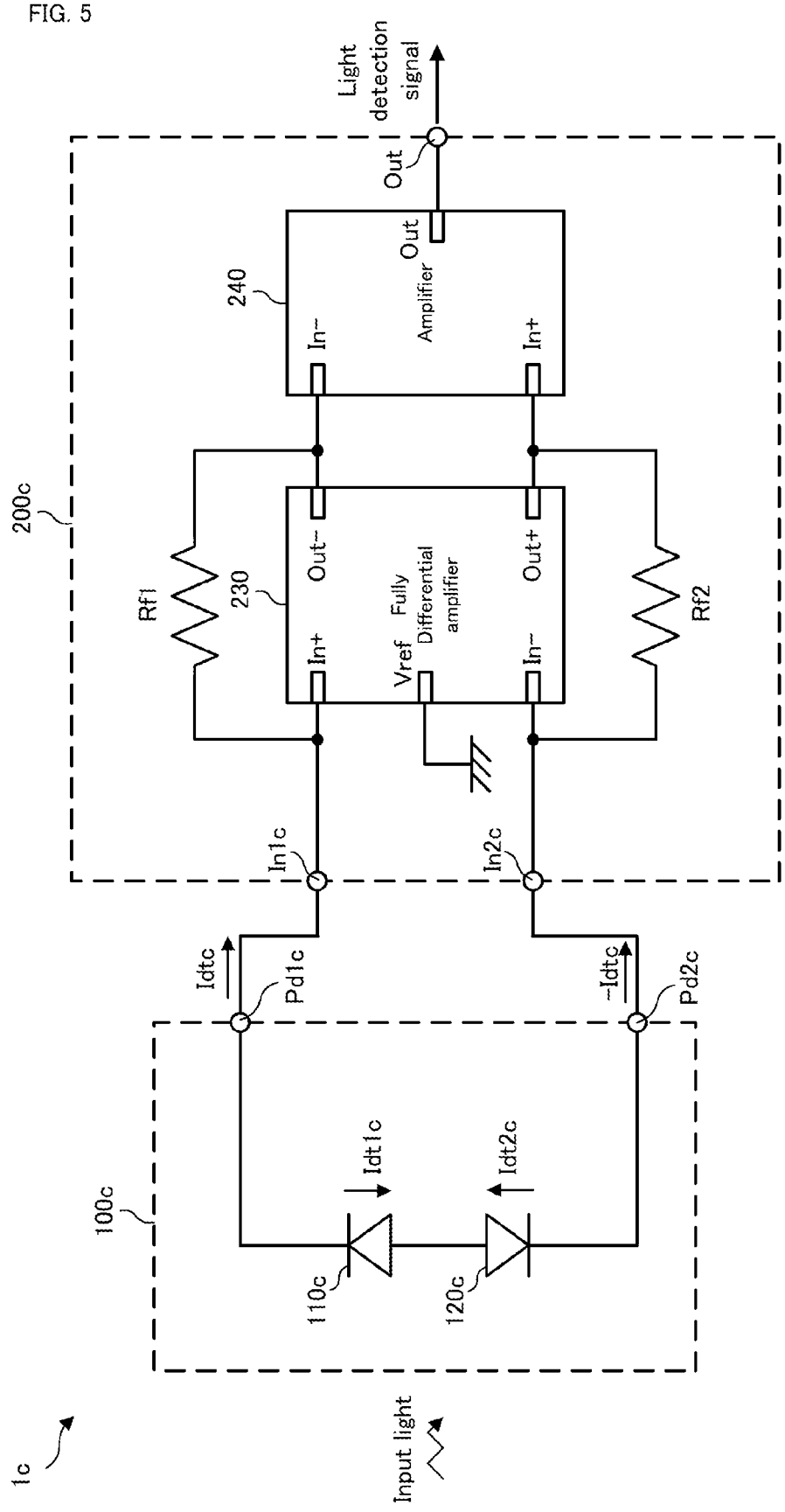
FIG. 5 is a block diagram showing a configuration of a light detecting apparatus in a third example.

FIG. 5 is a block diagram showing a configuration of the light detecting apparatus in the third example.

In FIG. 5, a light detecting apparatus 1c in the third example is a light detecting apparatus for detecting a signal light component included in input light inputted from the exterior, which is provided with: an optical current transducer unit 100c; and a current/voltage converting unit 200c. The input light is, for example, light obtained by that laser light is reflected, scattered, or the like by a test object, a specimen, or an object to be examined (e.g. a human finger, etc.) and includes the signal light component indicating information about the test object (e.g. a modulation component by the reflection, scattering, or the like in the test object).

In FIG. 5, the optical current transducer unit 100c has light receiving elements 110c and 120c and terminals Pd1c and Pd2c. Incidentally, the light receiving element 110c is one example of the "first photoelectric conversion element unit" of the present invention, and the light receiving element 120c is one example of the "second photoelectric conversion element unit" of the present invention.

Each of the light receiving elements 110c and 120c is a photodiode such as a PIN diode, receives the input light, and outputs an electric current in accordance with amount of the input light received. The light receiving elements 110c and 120c are connected in series such that anodes thereof are connected to each other. A cathode of the light receiving element 110c is connected to the terminal Pd1c, and a cathode of the light receiving element 120c is connected to the terminal Pd2c. Since the light receiving elements 110c and 120c are connected in series in this manner, the optical current transducer unit 100c can output a differential current (Idt2c-Idt1c) between an electric current Idt1c outputted by the light receiving element 110c and an electric current Idt2c outputted by the light receiving element 120c as a detected current Idtc from the terminal Pd1c. Moreover, the optical current transducer unit 100c can output from the terminal Pd2c an electric current (−Idtc) in which a polarity of the detected current Idtc outputted from the terminal Pd1c is reversed.

The terminals Pd1c and Pd2c are connected to input terminals In1c and In2c of the current/voltage converting unit 200c, respectively.

According to the current/voltage converting unit 200c configured in this manner, it is possible to cancel a DC component of the electric current Idt1c outputted by the light receiving element 110c and a DC component of the electric current Idt2c outputted by the light receiving element 120c, and it is possible to output the detected current Idtc mainly including an AC component corresponding to a signal light component included in the input light. As a result, it is possible to improve an S/N ratio in a light detection signal outputted by the current/voltage converting unit 200c.

The current/voltage converting unit 200c has: the input terminals In1c and In2c; a fully differential amplifier 230 as one example of the "fully differential amplifier" of the present invention; feedback resistors Rf1 and Rf2; an amplifier 240; and an output terminal Out. The fully differential amplifier 230 converts the electric current Idtc, which is inputted to the input terminal In1c, to a voltage signal −Rf1*Idtc and outputs it from an output terminal Out−. At the same time, the fully differential amplifier 230 converts the electric current −Idtc, which is inputted to the input terminal In2c, to a voltage signal Rf2*Idtc and outputs it from an output terminal Out+. In other words, the fully differential amplifier 230 is configured as a transimpedance amplifier for independently current/voltage-converting the electric currents inputted to the input terminals In1c and In2c and differentially outputting them.

The current/voltage converting unit 200c converts the detected current Idtc, which is inputted to the input terminal In1c from the optical current transducer unit 100c, to the voltage signal and outputs it as the light detection signal from the output terminal Out.

The fully differential amplifier 230 is a fully differential amplifier having: an input terminal In+ connected to the input terminal In1c; an input terminal In− connected to the input terminal In2c; the output terminal Out−; and the output terminal Out+. A reference potential is inputted via a reference potential terminal Vref. The Output terminals Out− and Out+ are connected to input terminals In− and In+ of the amplifier 240 described later, respectively.

The feedback resistor Rf1 is connected between the input terminal In+ of the fully differential amplifier 230 and the output terminal Out− of the fully differential amplifier 230, performs negative feedback and converts an electric current to a voltage. The feedback resistor Rf2 is connected between the input terminal In− of the fully differential amplifier 230 and the output terminal Out+ of the fully differential amplifier 230, performs negative feedback and converts an electric current to a voltage. Since the negative feedback is performed by the feedback resistors Rf1 and Rf2, a potential difference between the input terminal In+ and the reference potential terminal Vref of the fully differential amplifier 230 is almost zero. In the same manner, a potential difference between the input terminal In− and the reference potential terminal Vref is almost zero. As a result, the input terminal In+ and the input terminal In− have almost the same potential. Thus, a potential difference between the terminal Pd1c connected to the input terminal In+ of the fully differential amplifier 230 via the input terminal In1c and the terminal Pd2c connected to the input terminal In− of the fully differential amplifier 230 via the input terminal In2c is almost zero, and each of the light receiving elements 110c and 120c can be operated in a zero bias condition, i.e. in a so-called power generation mode. Therefore, it is possible to reduce or eliminate a dark current generated in the light receiving elements 110c and 120c. This makes it possible to reduce a noise current due to fluctuation of the dark current and to improve the S/N ratio in the light detection signal outputted by the current/voltage converting unit 200c.

The amplifier 240 is an amplifier for amplifying and outputting a potential difference 2*Rf*Idtc (selected such that Rf1=Rf2=Rf) between the voltage signal −Rf1*Idtc inputted from the input terminal In− and the voltage signal Rf2*Idtc inputted from the input terminal In+. An output terminal of the amplifier 240 is connected to the output terminal Out of the current/voltage converting unit 200c.

Figure 6:
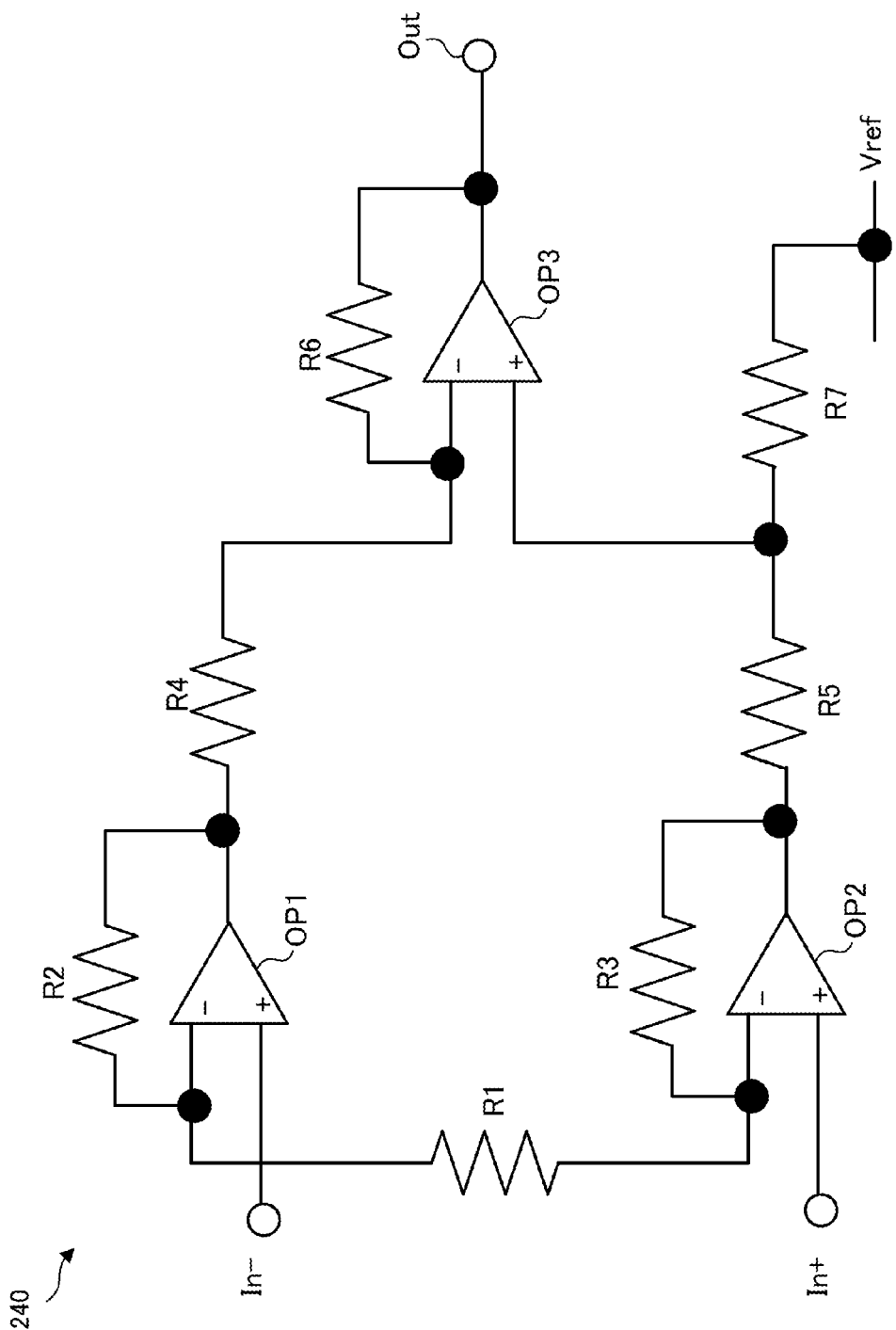
FIG. 6 is a circuit diagram showing a configuration of an amplifier provided for the light detecting apparatus in the third example.

FIG. 6 is a circuit diagram showing a configuration of the amplifier 240.

In FIG. 6, the amplifier 240 is configured as an instrumentation amplifier, and it is provided with: operational amplifiers OP1, OP2, and OP3; feedback resistors R2, R3, and R6; a common input resistor R1; and input resistors R4, R5, and R7.

The input terminal In− of the amplifier 240 is connected to a non-inverted input terminal (+) of the operational amplifier OP1. The input terminal In+ of the amplifier 240 is connected to a non-inverted input terminal (+) of the operational amplifier OP2. The operational amplifiers OP1 and OP2 are subject to negative feedback by the feedback resistors R2 and R3, respectively.

The feedback resistors R2 and R3 are set to have an equal resistance value.

The common input resistor R1 is connected between an inverted input terminal of the operational amplifier OP1 and an inverted input terminal of the operational amplifier OP2. Incidentally, the common input resistor R1 may function as a variable resistor for varying gain.

An output terminal of the amplifier OP1 is connected to an inverted input terminal of the operational amplifier OP3 via the input resistor R4. An output terminal of the operational amplifier OP2 is connected to a non-inverted input terminal of the operational amplifier OP3 via the input resistor R5. Between the input resistor R5 and the non-inverted input terminal of the operational amplifier OP3, one of terminals of the input resistor R7 is connected. The other terminal of the input resistor R7 is connected to the reference potential Vref, which is, for example, a GND potential. A voltage outputted from the operational amplifier OP2 is divided by the input resistors R5 and R7 and is inputted to the non-inverted input terminal of the operational amplifier OP3.

The input resistors R4 and R5 are set to have an equal resistance value.

The operational amplifier OP3 is subject to negative feedback by the feedback resistor R6. An output terminal of the operational amplifier OP3 is connected to the output terminal Out of the current/voltage converting unit 200c.

The feedback resistor R6 and the input resistor R7 are set to have an equal resistance value.

According to the amplifier 240 configured in this manner, in-phase components (e.g. hum noise) in the two voltage signals respectively outputted from the output terminal Out− and Out+ of the fully differential amplifier 230 can be removed as noise. Moreover, the two voltage signals respectively outputted from the output terminal Out− and Out+ of the fully differential amplifier 230 are two differential signals which are differentially outputted in accordance with the detected current Idtc and which are different in polarity. Thus, to the input terminals In+ and In− of the amplifier 240, the signal light component of the detected light is inputted in reverse phase. By this, the in-phase components such as hum noise can be removed as the noise from a voltage signal outputted as a light detection signal by the amplifier 240. In addition, since the signal light component of the detected light is reversed-phase, it is amplified by the amplifier 240 and is outputted as the light detection signal. As a result, since the noise component can be reduced and the signal light component can be increased in the light detection signal, the S/N ratio can be significantly improved.

Fourth Example

A light detecting apparatus in a fourth example will be explained with reference to FIG. 7.

The light detecting apparatus in the fourth example is different from the light detecting apparatus 1c in the third example described above in that there is provided an amplifier 240d instead of the amplifier 240 in the third example described above with reference to FIG. 5 and FIG. 6; however, in other points, the light detecting apparatus in the fourth example is configured in substantially the same manner as the light detecting apparatus 1c in the third example described above.

Figure 7:
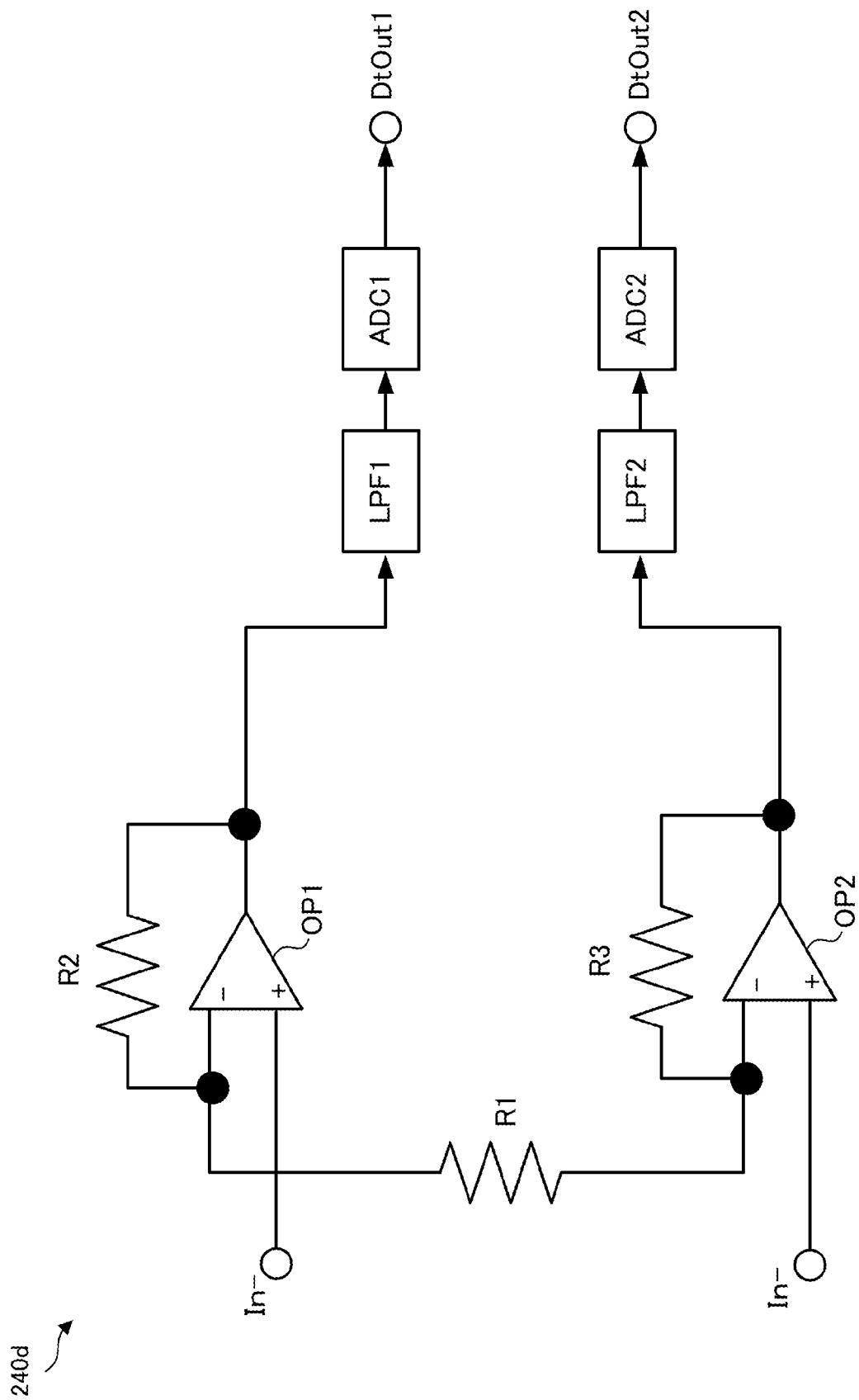
FIG. 7 is a circuit diagram showing a configuration of an amplifier provided for a light detecting apparatus in a fourth example.

FIG. 7 is a circuit diagram showing a configuration of the amplifier in the fourth example. Incidentally, in FIG. 7, the same constituents as those in the third example shown in FIG. 5 and FIG. 6 will carry the same reference numerals, and the explanation thereof will be omitted, as occasion demands.

In FIG. 7, the amplifier 240d is provided with: operational amplifiers OP1 and OP2; feedback resistors R2 and R3; a common input resistor R1; low pass filters (i.e. low-frequency pass filters) LPF1 and LPF2, and Analog to Digital (AD) converters ADC1 and ADC2.

The amplifier 240 in the third example described above with reference to FIG. 5 and FIG. 6 can output the light detection signal as a single end signal and as an analog signal. In contrast, as shown in FIG. 7, the amplifier 240d in the example is configured to output two differential signals which are different in polarity, as light detection signals DtOut1 and DtOut2. In addition, the light detection signals DtOut1 and DtOut2 are outputted as digital signals via the low pass filters LPF1 and LPF2 and the AD converters ADC1 and ADC2, respectively. According to the amplifier 240d, an output signal of the operational amplifier OP1 is inputted to the AD converter ADC1 via the low pass filter LPF1 as an anti aliasing filter (i.e. a filter capable of removing aliasing noise generated by sampling performed by the AD converter) and an output signal of the operational amplifier OP2 is inputted to the AD converter ADC2 via the low pass filter LPF2 as an anti aliasing filter. Thus, the S/N ratio can be increased in each of the light detection signals DtOut1 and DtOut2. With regard to the light detection signals DtOut1 and DtOut2 which are output signals of the AD converters ADC1 and ADC2 and which are quantized, a subtraction process may be performed by a signal processing apparatus (not illustrated) such as a digital signal processing apparatus like a Digital Signal Processor (DSP).

As a result, according to the example, since the light detection signals DtOut1 and DtOut2 are quantized, it is resistant to noise from an outer world environment in the case of transmission performed via a communication network. Thus, it is possible to realize long distance transmission of the light detection signal.

Fifth Example

A blood flow measuring apparatus in a fifth example will be explained with reference to FIG. 8.

Figure 8:
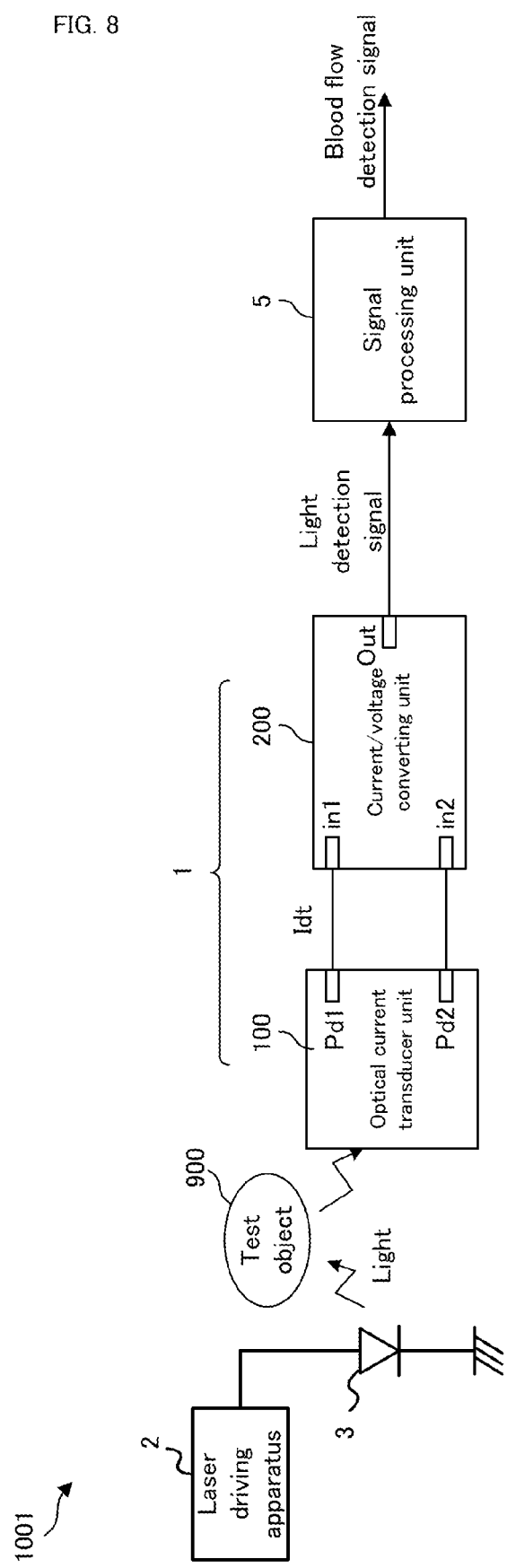
FIG. 8 is a block diagram showing a configuration of a blood flow measuring apparatus in a fifth example.

FIG. 8 is a block diagram showing a configuration of the blood flow measuring apparatus in the fifth example. Incidentally, in FIG. 8, the same constituents as those in the first example shown in FIG. 1 and FIG. 2 will carry the same reference numerals, and the explanation thereof will be omitted, as occasion demands.

In FIG. 8, a blood flow measuring apparatus 1001 in the example is one example of the "fluid measuring apparatus" of the present invention, and is an apparatus for measuring volume of blood flow of a test object 900 which is a living body.

The blood flow measuring apparatus 1001 is provided with: a laser driving apparatus 2; a semiconductor laser 3; the light detecting apparatus 1 in the first example described above with reference to FIG. 1 and FIG. 2; and a signal processing unit 5. Incidentally, the laser driving apparatus 2 and the semiconductor laser 3 are one example of the "irradiating unit" of the present invention, and the signal processing unit 5 is one example of the "calculating unit" of the present invention.

In FIG. 8, the semiconductor laser 3 is driven by the laser driving apparatus 2, by which light from the semiconductor laser 3 is applied or irradiated to the test object 900. The light applied to the test object 900 is reflected or scattered by hemoglobin in blood capillaries of the test object 900. The light reflected or scattered in the test object 900 enters the optical current transducer unit 100 of the light detecting apparatus 1 (more specifically, the light receiving elements 110 and 120 described above with reference to FIG. 2). In accordance with the entering light, a detected current Idt is outputted from the optical current transducer unit 100. The detected current Idt is converted to a voltage signal by the current/voltage converting unit 200 and is inputted to the signal processing unit 5 as a light detection signal. The signal processing unit 5 calculates the volume of blood flow on the basis of the inputted light detection signal and outputs a digital signal including the volume of blood flow as a blood flow detection signal.

Here, in particular, since the blood flow measuring apparatus 1001 is provided with the light detecting apparatus 1 in the first example described above, the volume of blood flow can be calculated by the signal processing unit 5 on the basis of the light detection signal with a high S/N ratio. Thus, the volume of blood flow can be calculated accurately.

Incidentally, the blood flow measuring apparatus may further provided with: two light detecting apparatuses each of which is configured in the same manner as the light detecting apparatus 1 in the first example described above; and a signal processing unit for calculating the volume of blood flow on the basis of a difference between light detection signals respectively outputted from the two light detecting apparatuses and for outputting a digital signal indicating the volume of blood flow as a blood flow detection signal. By virtue of such a configuration, in-phase components such as hum noise can be removed more certainly, and the volume of blood flow can be calculated more accurately.

Sixth Example

A blood flow measuring apparatus in a sixth example will be explained with reference to FIG. 9.

Figure 9:
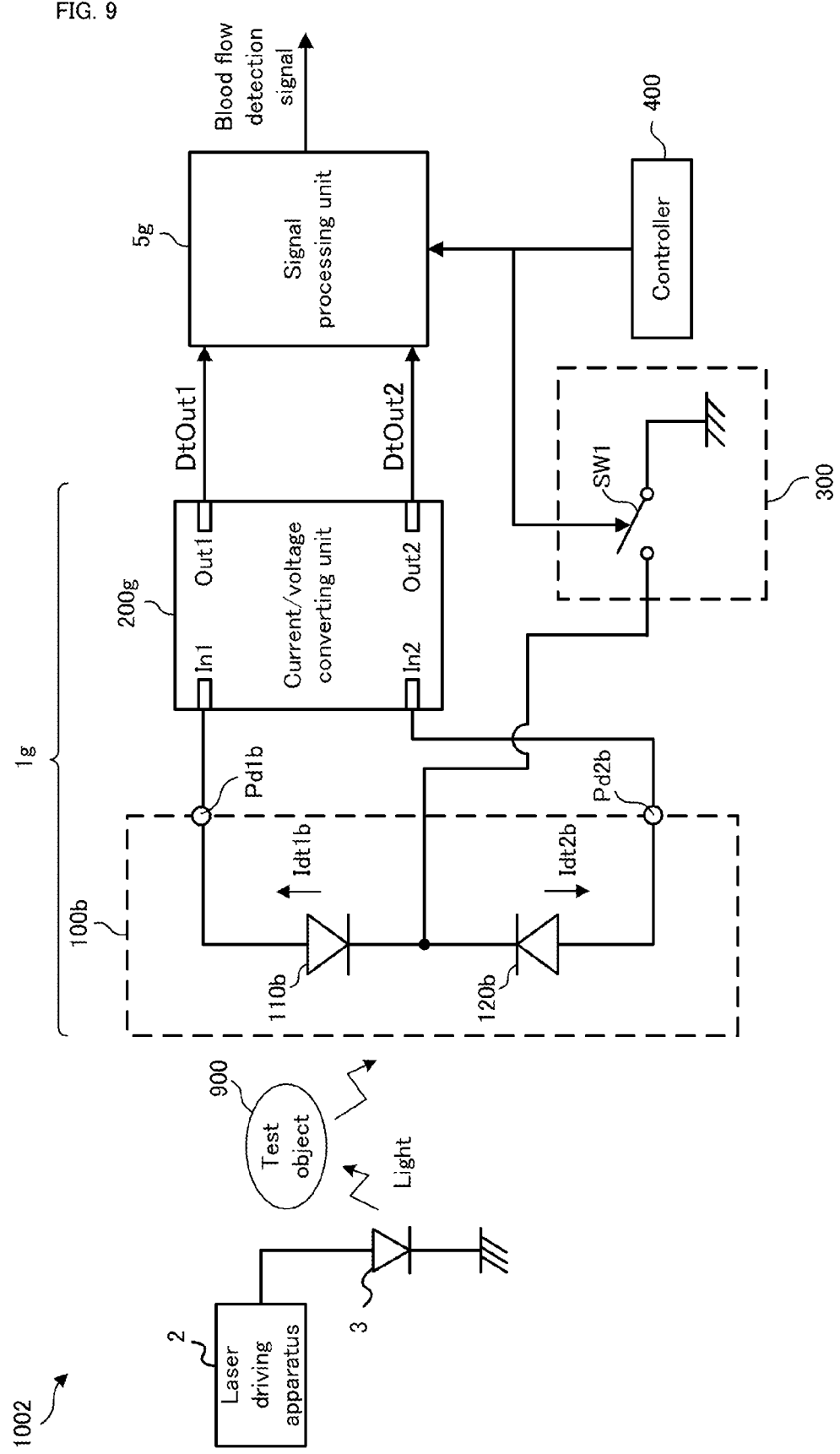
FIG. 9 is a block diagram showing a configuration of a blood flow measuring apparatus in a sixth example.

FIG. 9 is a block diagram showing a configuration of the blood flow measuring apparatus in the sixth example. Incidentally, in FIG. 9, the same constituents as those in the second example shown in FIG. 4 and those in the fifth example shown in FIG. 8 will carry the same reference numerals, and the explanation thereof will be omitted, as occasion demands.

In FIG. 9, a blood flow measuring apparatus 1002 in the example is one example of the "fluid measuring apparatus" of the present invention, and is an apparatus for measuring volume of blood flow of a test object 900 which is a living body.

The blood flow measuring apparatus 1002 is provided with: a laser driving apparatus 2; a semiconductor laser 3; a light detecting apparatus 1g; and a signal processing unit 5g.

The light detecting apparatus 1g is provided with: an optical current transducer unit 100b; and a current/voltage converting unit 200g.

The optical current transducer unit 100b has light receiving elements 110b and 120b which are connected in series such that cathodes thereof are connected to each other. An anode of the light receiving element 110b is connected to an input terminal In1 of the current/voltage converting unit 200g via a terminal Pd1b, and an anode of the light receiving element 120b is connected to an input terminal In2 of the current/voltage converting unit 200g via a terminal Pd2b.

In the example, in particular, one end of a bias application selecting element 300 is connected between the light receiving elements 110b and 120b. The bias application selecting element 300 selects whether or not a bias voltage is applied to the light receiving elements 110b and 120b on the basis of a command from a controller 400. The bias application selecting element 300 is provided with an analog switch SW1. One end of the analog switch SW1 is connected between the light receiving elements 110b and 120b (i.e. at a connection point between the light receiving elements 110b and 120), and the other end of the analog switch SW1 is connected to a bias potential such as a GND potential. The bias application selecting element 300 switches between ON and OFF of the analog switch SW1 in accordance with the command from the controller 400, thereby selecting whether or not the bias voltage is applied to the light receiving elements 110b and 120b. Incidentally, the bias application selecting element 300 and the controller 400 are one example of the "bias application applying device" of the present invention.

The current/voltage converting unit 200g is configured in substantially the same manner as the current/voltage converting unit provided for the light detecting apparatus described above with reference to FIG. 7. In other words, the current/voltage converting unit 200g is provided with: a fully differential amplifier 230 (refer to FIG. 5); feedback resistors Rf1 and Rf2 (refer to FIG. 5); and an amplifier 240d (refer to FIG. 7). The current/voltage converting unit 200g outputs light detection signals DtOut1 and DtOut2 from output terminals Out1 and Out2.

The signal processing unit 5g calculates the volume of blood flow on the basis of the inputted light detection signals DtOut1 and DtOut2 and outputs a digital signal indicating the volume of blood flow as a blood flow detection signal. The signal processing unit 5g changes the content of signal processing between at the time of bias application at which the bias voltage is applied to the light receiving elements 110b and 120b on the basis of the command from the controller 400 (i.e. when the analog switch SW1 is set to be ON) and at the time of opening at which the bias voltage is not applied to the light receiving elements 110b and 120b (when the analog switch SW1 is set to be OFF).

Specifically, at the time of bias application, the signal processing unit 5g adds the inputted light detection signals DtOut1 and DtOut2, thereby calculating a DC light power component. On the other hand, at the time of opening, the signal processing unit 5g subtracts the inputted light detection signals DtOut1 and DtOut2, thereby calculating a power spectrum of a signal light component of a beat signal or the like and calculating the volume of blood flow of the test object 900 on the basis of the power spectrum. Moreover, the signal processing unit 5g carries out standardization by dividing the volume of blood flow calculated at the time of opening by the DC light power component calculated at the time of bias application. This makes it possible to accurately measure the volume of blood flow of the test object 900 even if power fluctuation occurs in light emitted from the semiconductor laser 3.

Seventh Example

A blood flow measuring apparatus in a seventh example will be explained with reference to FIG. 10.

Figure 10:
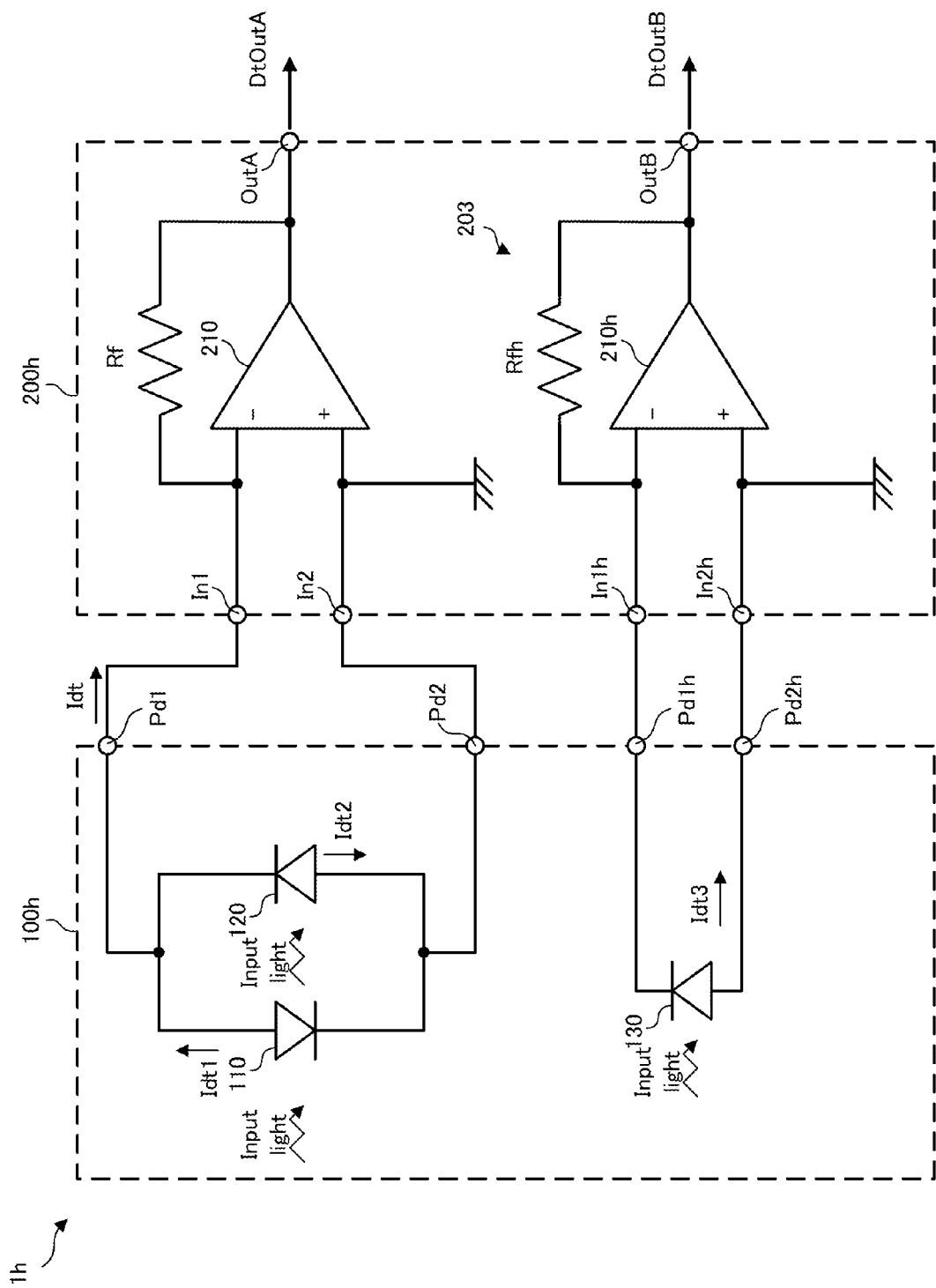
FIG. 10 is a circuit diagram showing a configuration of a light detecting apparatus in a seventh example.

FIG. 10 is a block diagram showing a configuration of the blood flow measuring apparatus in the seventh example. Incidentally, in FIG. 10, the same constituents as those in the first example shown in FIG. 2 will carry the same reference numerals, and the explanation thereof will be omitted, as occasion demands.

In FIG. 10, a light detecting apparatus 1h in the seventh example is different from the light detecting apparatus 1 in the first example described above in that there are further provided a light receiving element 130 and a current/voltage converting potion 203 for converting an electric current, which is outputted from the light receiving element 130, to a voltage; however, in other points, the light detecting apparatus 1h is configured in substantially the same manner as the light detecting apparatus 1 in the first example described above. Incidentally, the light receiving element 130 is one example of the "third photoelectric conversion element unit" of the present invention, and the current/voltage converting potion 203 is one example of the "second current/voltage converting unit" of the present invention.

In FIG. 10, the light detecting apparatus 1h in the seventh example is provided with: an optical current transducer unit 100h; and a current/voltage converting unit 200h.

The optical current transducer unit 100h has: light receiving elements 110 and 120 which are connected in parallel; and terminals Pd1 and Pd2, as in the optical current transducer unit 100 in the first example described above. Moreover, the optical current transducer unit 100h has: the light receiving element 130 provided separately from the light receiving elements 110 and 120; and terminals Pd1h and Pd2h. The light receiving element 130 is a photodiode such as a PIN diode, receives input light, and outputs an electric current in accordance with amount of the input light received. A cathode of the light receiving element 130 is connected to the terminal Pd1h, and an anode of the light receiving element 130 is connected to the terminal Pd2h.

The terminals Pd1h and Pd2h are connected to input terminals In1h and In2h of the current/voltage converting unit 200h described later, respectively.

The current/voltage converting unit 200h has: input terminals In1 and In2; an operational amplifier 210; a feedback resistor Rf; and an output terminal OutA, in substantially the same manner as the current/voltage converting unit 200 in the first example described above. Incidentally, the output terminal OutA is connected to an output terminal of the operational amplifier 210. The output terminal OutA outputs a voltage signal outputted from the operational amplifier 210 as a light detection signal DtOutA.

Moreover, the current/voltage converting unit 200h has the current/voltage converting potion 203 for converting the electric current, which is outputted from the light receiving element 130, to the voltage. The current/voltage converting potion 203 has: the input terminals In1h and In2h; an operational amplifier 210h; a feedback resistor Rfh; and an output terminal OutB.

The input terminal In1h is connected to an inverted input terminal (−) of the operational amplifier 210h. The input terminal In2h is connected to a non-inverted input terminal (+) of the operational amplifier 210h. The input terminal In2h and the non-inverted terminal of the operational amplifier 210h are grounded.

The feedback resistor Rfh is connected between an output terminal of the operational amplifier 210h and the inverted input terminal of the operational amplifier 210h, performs negative feedback, and converts an electric current to a voltage. Since the negative feedback is performed by the feedback resistor Rfh, a potential difference between the inverted input terminal and the non-inverted input terminal of the operational amplifier 210h is almost zero (i.e. a so-called "imaginary short" is realized).

The output terminal OutB is connected to the output terminal of the operational amplifier 210h. The output terminal OutB outputs a voltage signal outputted from the operational amplifier 210h as a light detection signal DtOutB.

As described above, particularly in the example, since the light detecting apparatus 1h is provided with: the light receiving element 130; and the current/voltage converting portion 203 for converting the electric current, which is outputted from the light receiving element 130, to the voltage, a signal corresponding to a fixed light component of input light can be outputted as the light detection signal DtOutB on the basis of an electric current Idt3 outputted by the light receiving element 130. Thus, it is possible to carry out signal standardization by dividing the light detection signal DtOutA based on a detected current Idt from the light receiving elements 110 and 120 which are connected in parallel (i.e. a signal corresponding to a signal light component of the input light) by the light detection signal DtOutB (the signal corresponding to the fixed light component of the input light). Thus, it is possible to accurately detect the signal light component included in the input light even if power fluctuation occurs in light emitted from a light source.

The present invention is not limited to the aforementioned embodiments, but various changes may be made, if desired, without departing from the essence or spirit of the invention which can be read from the claims and the entire specification. A light detecting apparatus and a fluid measuring apparatus, which involve such changes, are also intended to be within the technical scope of the present invention.

DESCRIPTION OF REFERENCE CODES 1, 1b, 1c, 1g, 1h light detecting apparatus
2 laser driving apparatus
3 semiconductor laser
5, 5g signal processing unit
100, 100b, 100c, 100g, 100h optical current transducer unit
110, 120, 110b, 120b, 110c, 120c light receiving element
200, 200c, 200g, 200h current/voltage converting unit
210, 210h operational amplifier
230 fully differential amplifier
240, 240d amplifier
300 bias application selecting element
400 controller
1001, 1002 blood flow measuring apparatus
Rf, Rfh, Rf1, Rf2 feedback resistor
SW1 analog switch

The invention claimed is:
1. A light detecting apparatus for detecting a signal light component included in input light, said light detecting apparatus comprising:

an optical current transducer unit which includes first and second photoelectric conversion element units each converting the input light to an electric current and outputting it, and which outputs a differential current between an electric current outputted by the first photoelectric conversion element unit and an electric current outputted by the second photoelectric conversion element unit as a detected current; and a first current/voltage converting unit which amplifies the detected current outputted from said optical current transducer unit, converts it to a voltage signal, and outputs the voltage signal, wherein the first and second photoelectric conversion element units are connected in series such that cathodes thereof or anode thereof are connected to each other, and a connection point between the first and second photoelectric conversion element units connected in series is floating.

2. The light detecting apparatus according to claim 1, wherein said optical current transducer unit has first and second terminals which are connected to both ends of the first and second photoelectric conversion element units, respectively, and said first current/voltage converting unit has:

a fully differential amplifier having a positive input terminal connected to the first terminal, a negative input terminal connected to the second terminal, a negative output terminal for inverting, amplifying, and outputting a signal inputted to the positive input terminal, and a positive output terminal for inverting, amplifying, and outputting a signal inputted to the negative input terminal;

a first negative feedback resistor connected between the positive input terminal and the negative output terminal;

a second negative feedback resistor connected between the negative input terminal and the positive output terminal; and an amplifier for amplifying a difference between a signal outputted from the positive output terminal and a signal outputted from the negative output terminal and for outputting it as a voltage signal.

3. A fluid measuring apparatus comprising:

an irradiating unit for irradiating a test object with light;

said light detecting apparatus according to claim 1, to which light from the test object due to the irradiated light is inputted as the input light; and a calculating unit for calculating fluid information about a fluid in the test object on the basis of the voltage signal outputted by said first current/voltage converting unit.

4. A fluid measuring apparatus comprising:

an irradiating unit for irradiating a test object with light;

said light detecting apparatus according to claim 2, to which light from the test object due to the irradiated light is inputted as the input light; and a calculating unit for calculating fluid information about a fluid in the test object on the basis of the voltage signal outputted by said first current/voltage converting unit.

5. A light detecting apparatus for detecting a signal light component included in input light, said light detecting apparatus comprising:

an optical current transducer unit which includes first and second photoelectric conversion element units each converting the input light to an electric current and outputting it, and which outputs a differential current between an electric current outputted by the first photoelectric conversion element unit and an electric current outputted by the second photoelectric conversion element unit as a detected current; and a first current/voltage converting unit which amplifies the detected current outputted from said optical current transducer unit, converts it to a voltage signal, and outputs the voltage signal, wherein the first and second photoelectric conversion element units are connected in series such that cathodes thereof or anode thereof are connected to each other, said light detecting apparatus further comprises a bias voltage applying device which is connected between the first and second photoelectric conversion element units connected in series and which can apply a bias voltage to each of the first and second photoelectric conversion element units, and said optical current transducer unit outputs each of the electric current outputted by the first photoelectric conversion element unit and the electric current outputted by the second photoelectric conversion element unit if the bias voltage is applied to each of the first and second photoelectric conversion element units by said bias voltage applying device.

6. The light detecting apparatus according to claim 5, wherein said optical current transducer unit has first and second terminals which are connected to both ends of the first and second photoelectric conversion element units, respectively, and said first current/voltage converting unit has:

a fully differential amplifier having a positive input terminal connected to the first terminal, a negative input terminal connected to the second terminal, a negative output terminal for inverting, amplifying, and outputting a signal inputted to the positive input terminal, and a positive output terminal for inverting, amplifying, and outputting a signal inputted to the negative input terminal;

a first negative feedback resistor connected between the positive input terminal and the negative output terminal;

a second negative feedback resistor connected between the negative input terminal and the positive output terminal; and an amplifier for amplifying a difference between a signal outputted from the positive output terminal and a signal outputted from the negative output terminal and for outputting it as a voltage signal.

7. A fluid measuring apparatus comprising:

an irradiating unit for irradiating a test object with light;

said light detecting apparatus according to claim 5, to which light from the test object due to the irradiated light is inputted as the input light; and a calculating unit for calculating fluid information about a fluid in the test object on the basis of the voltage signal outputted by said first current/voltage converting unit.

8. A light detecting apparatus for detecting a signal light component included in input light, said light detecting apparatus comprising:

an optical current transducer unit which includes first and second photoelectric conversion element units each converting the input light to an electric current and outputting it, and which outputs a differential current between an electric current outputted by the first photoelectric conversion element unit and an electric current outputted by the second photoelectric conversion element unit as a detected current;

a first current/voltage converting unit which amplifies the detected current outputted from said optical current transducer unit, converts it to a voltage signal, and outputs the voltage signal;

a third photoelectric conversion element unit for converting the input light to an electric current and outputting it; and a second current/voltage converting unit for amplifying the electric current outputted from said third photoelectric conversion element unit and converting it to a voltage signal, wherein an AC signal, which is an output of said first current/voltage converting unit, is standardized by a DC signal, which is an output of said second current/voltage converting unit.

9. The light detecting apparatus according to claim 8, wherein said optical current transducer unit has first and second terminals which are connected to both ends of the first and second photoelectric conversion element units, respectively, and said first current/voltage converting unit has:

a fully differential amplifier having a positive input terminal connected to the first terminal, a negative input terminal connected to the second terminal, a negative output terminal for inverting, amplifying, and outputting a signal inputted to the positive input terminal, and a positive output terminal for inverting, amplifying, and outputting a signal inputted to the negative input terminal;

a first negative feedback resistor connected between the positive input terminal and the negative output terminal;

a second negative feedback resistor connected between the negative input terminal and the positive output terminal; and an amplifier for amplifying a difference between a signal outputted from the positive output terminal and a signal outputted from the negative output terminal and for outputting it as a voltage signal.

10. A fluid measuring apparatus comprising:

an irradiating unit for irradiating a test object with light;

said light detecting apparatus according to claim 8, to which light from the test object due to the irradiated light is inputted as the input light; and a calculating unit for calculating fluid information about a fluid in the test object on the basis of the voltage signal outputted by said first current/voltage converting unit.

* * * * *